United States Patent
Glottmann et al.

(10) Patent No.: US 11,380,432 B2
(45) Date of Patent: Jul. 5, 2022

(54) SYSTEMS AND METHODS FOR IMPROVED ANALYSIS AND GENERATION OF MEDICAL IMAGING REPORTS

(71) Applicant: IMEDIS AI LTD, Hod Hasharon (IL)

(72) Inventors: Tomer Glottmann, Hod Hasharon (IL); Shmuel Yitzhak Pfeffer, Lod (IL); Aviel Blumenfeld, Bitzaron (IL)

(73) Assignee: IMEDIS AI LTD, Hod Hasharon (IL)

( * ) Notice: Subject to any disclaimer, the term of this patent is extended or adjusted under 35 U.S.C. 154(b) by 109 days.

(21) Appl. No.: 16/529,842

(22) Filed: Aug. 2, 2019

(65) Prior Publication Data
US 2020/0043600 A1 Feb. 6, 2020

Related U.S. Application Data

(60) Provisional application No. 62/713,557, filed on Aug. 2, 2018.

(51) Int. Cl.
*G16H 30/20* (2018.01)
*G06T 7/00* (2017.01)
(Continued)

(52) U.S. Cl.
CPC ............ *G16H 30/20* (2018.01); *G06F 40/20* (2020.01); *G06N 3/08* (2013.01); *G06T 7/0012* (2013.01);
(Continued)

(58) Field of Classification Search
CPC ......... G06F 40/20; G06N 3/0445; G06N 3/08
See application file for complete search history.

(56) References Cited

U.S. PATENT DOCUMENTS

2008/0247676 A1* 10/2008 Minakuchi ............ G16H 15/00
382/305
2009/0132499 A1 5/2009 Yamagishi et al.
(Continued)

FOREIGN PATENT DOCUMENTS

WO 20140365232 A1 3/2011
WO 2013075127 A1 5/2013
(Continued)

OTHER PUBLICATIONS

U.S. Appl. No. 16/908,016 dated Oct. 23, 2020, 40 pages.
(Continued)

*Primary Examiner* — Reginald R Reyes
(74) *Attorney, Agent, or Firm* — DLA Piper LLP US

(57) ABSTRACT

Systems and methods for the improved analysis and generation of medical imaging reports are disclosed. In particular, the present disclosure provides systems and methods that may be used for the automated analysis of radiological information, such as medical images and related text statements for discrepancy analysis, accuracy analysis and quality assurance. Systems and methods may include receiving medical images and textual data, generating enhanced medical image data by applying an artificial intelligence module to the received medical images, generating structured text data by applying a natural language processing module to the received textual data, and generating improved medical image reports and/or alerts based on the generated enhanced medical image data and the generated structured text data.

14 Claims, 10 Drawing Sheets

(51) Int. Cl.
*G16H 30/40* (2018.01)
*G16H 15/00* (2018.01)
*G06N 3/08* (2006.01)
*G16H 50/20* (2018.01)
*G06F 40/20* (2020.01)

(52) U.S. Cl.
CPC ............. *G16H 15/00* (2018.01); *G16H 30/40* (2018.01); *G16H 50/20* (2018.01); *G06T 2207/10081* (2013.01); *G06T 2207/10088* (2013.01); *G06T 2207/10116* (2013.01); *G06T 2207/20081* (2013.01); *G06T 2207/20084* (2013.01)

(56) References Cited

U.S. PATENT DOCUMENTS

| | | |
|---|---|---|
| 2012/0203575 A1 | 8/2012 | Tulipano et al. |
| 2014/0072192 A1 | 3/2014 | Reiner |
| 2014/0365232 A1 | 12/2014 | Sadeghi |
| 2016/0361025 A1 | 12/2016 | Reicher et al. |
| 2016/0361121 A1 | 12/2016 | Reicher et al. |
| 2016/0364526 A1 | 12/2016 | Reicher et al. |
| 2016/0364527 A1 | 12/2016 | Reicher et al. |
| 2016/0364528 A1 | 12/2016 | Reicher et al. |
| 2016/0364539 A1 | 12/2016 | Reicher et al. |
| 2016/0364630 A1 | 12/2016 | Reicher et al. |
| 2016/0364631 A1 | 12/2016 | Reicher et al. |
| 2016/0364857 A1 | 12/2016 | Reicher et al. |
| 2016/0364862 A1 | 12/2016 | Reicher et al. |
| 2017/0213112 A1* | 7/2017 | Sachs ................. G06N 3/08 |
| 2017/0293725 A1* | 10/2017 | Liu .................. G06F 16/24522 |
| 2017/0337329 A1 | 11/2017 | Liu et al. |
| 2018/0060512 A1 | 3/2018 | Sorenson et al. |
| 2018/0101645 A1 | 4/2018 | Sorenson et al. |
| 2018/0137244 A1* | 5/2018 | Sorenson ............. G16H 30/40 |
| 2018/0204325 A1 | 7/2018 | Steigauf et al. |
| 2018/0233222 A1* | 8/2018 | Daley ................ A61B 34/30 |
| 2018/0374245 A1* | 12/2018 | Xu ..................... G06T 11/005 |
| 2019/0138888 A1 | 5/2019 | Sekiyama et al. |
| 2022/0020495 A1 | 1/2022 | Sadeghi |

FOREIGN PATENT DOCUMENTS

| | | | |
|---|---|---|---|
| WO | 2019160557 A1 | 8/2019 | |
| WO | WO-2019160557 A1 * | 8/2019 | ............... G06N 3/08 |

OTHER PUBLICATIONS

U.S. Appl. No. 16/908,016, Office Action dated Mar. 12, 2021, 32 pages.
PCT International Application No. PCT/IB19/00926, Written Opinion of The International Searching Authority, dated Feb. 5, 2020, 5 pages.
PCT International Application No. PCT/IB19/00926, International Search Report of The International Searching Authority, dated Feb. 5, 2020, 2 pages.
U.S. Appl. No. 16/908,016, Office Action dated Oct. 5, 2021, 30 pages.
Examination Report in Indian Application No. 202117007307, dated Feb. 25, 2022, 7 pages.
U.S. Appl. No. 16/908,016, Office Action dated Mar. 17, 2022, 33 pages.
Extended European Search Report in International Application No. 19844646.0, dated Mar. 28, 2022, 12 pages.
Reiner, "Redefining the Practice of Peer Review in Intelligent Automation—Part 3: Automated Report Analysis and Data Reconciliation", J Digit Imaging, vol. 31, pp. 1-4, Jul. 25, 2017.

* cited by examiner

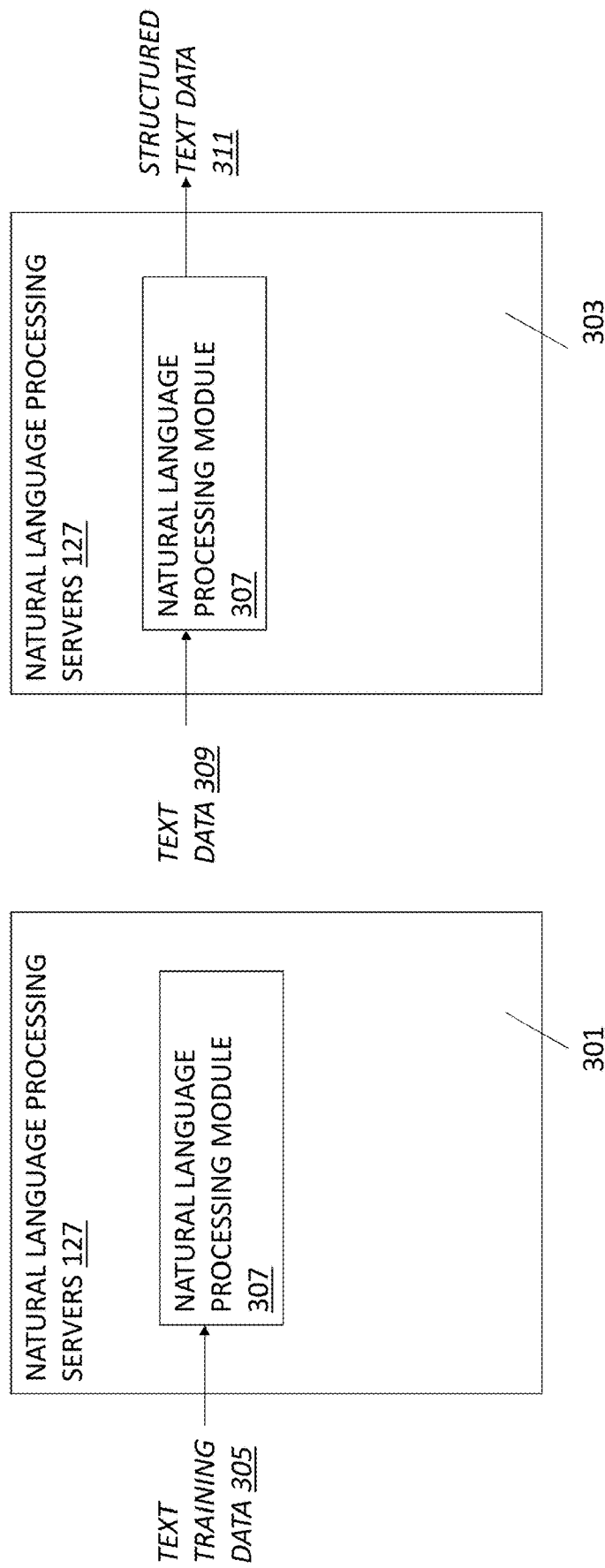

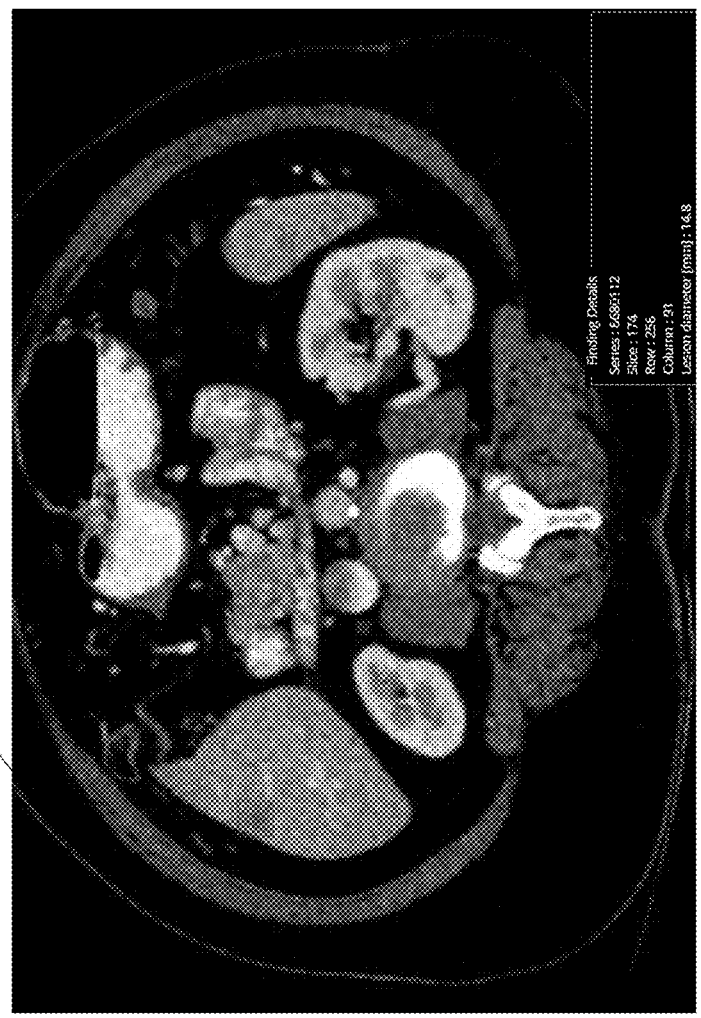
FIG. 8

FIG. 9

SYSTEMS AND METHODS FOR IMPROVED ANALYSIS AND GENERATION OF MEDICAL IMAGING REPORTS

CROSS-REFERENCE TO RELATED APPLICATIONS

This application claims the benefit of U.S. Provisional Application No. 62/713,557, filed Aug. 2, 2019, which is incorporated by reference in its entirety.

TECHNICAL FIELD

The present disclosure relates to systems and methods for the improved analysis and generation of medical imaging reports.

BACKGROUND

Medical imaging may involve the use of magnetic resonance imaging (MRI), computed tomography (CT), ultrasound, nuclear medicine, X-ray exams and the like. Medical images are commonly analyzed and interpreted by radiologists. However, in conventional systems the analysis and interpretation of medical images is often a manual process. For example, a radiologist manually locates the areas and regions of interest and prepares a written report. The written report is then sent to the referring physician. Commonly, the written report is integrated into an electronic health record.

Typically, a radiologists' interpretation of medical images is subjective. The accuracy of a radiologists' interpretation of a medical image is often dependent on factors such as (1) training, (2) experience, (3) expertise, and (4) time available to review a medical image. These factors often impact the accuracy and consistency of a radiologists' interpretation. Further, the time available to review a medical image may decrease as the number of conducted scans continues to increase and outpaces the number of radiologists. Additionally, the improvement in medical imaging technology may produce higher resolution imagery which requires more review time from radiologists, both of which places additional time pressures on radiologists.

In conventional systems, a radiologists' interpretation is sent to the referring physician and usually no other processes occur on the analyzed images to verify accuracy and quality of interpretation. The images and report are archived and remain unreviewed.

Further, rarely are the medical images or report analyzed to verify accuracy and quality of a radiologists' interpretation. In typical clinical settings, a manual peer-review (i.e., another peer radiologist reviews the case) is conducted on a small percentage of the annual case workload. Additionally, manual peer-review is conducted not as a measure for detecting missed findings, but as a method for understanding the general level of quality in the radiology department.

It is estimated that up to 30% of radiologist reports may suffer from errors including misinterpretation (and misdiagnosis) of medical images. Additionally, it is estimated that up to 60% of incidental findings (i.e., an incidentally discovered mass or lesion that is detected in a medical image performed for an unrelated primary objective) may be missed. Further, as radiologists are commonly focused on answering the "reason for study" and interpret only a section of the images, there is a missed potential for early-stage detection in imaging.

SUMMARY

The present disclosure is related to systems and methods for the improved analysis and generation of medical imaging reports. In particular, the present disclosure provides systems and methods that may be used for the automated analysis of radiological information, such as medical images and related text statements for discrepancy analysis, accuracy analysis and quality assurance. Accordingly, the analysis and generation of medical imaging reports may be improved. Further, the analysis and generation of electronic health records that integrate medical imaging reports may also be improved.

Embodiments of the present disclosure may include a method for generating improved medical image reports having the steps of: receiving medical images and textual data, generating enhanced medical image data by applying an artificial intelligence module to the received medical images, generating structured text data by applying a natural language processing module to the received textual data, and generating improved medical image reports based on the generated enhanced medical image data and the generated structured text data.

Embodiments of the present disclosure may also include a method for generating improved medical image reports including the steps of: receiving medical images and textual data, generating enhanced medical image data by applying an artificial intelligence module to the received medical images, generating structured text data by applying a natural language processing module to the received textual data, determining discrepancies between a received medical image report and the generated enhanced medical image data and the generated structured text data, and providing an alert to at least one of a user or a creator of the medical image report responsive to determining a discrepancy.

Optionally, applying an artificial intelligence module may include applying a convolutional neural network. Additionally, the method may include training at least a regression convolutional neural network, a semantic segmentation convolutional network and a classification convolutional neural network. Applying a natural language processing module to the received textual data may include applying a recurrent neural network. Generating the clinical or non-clinical interface may include the generated enhanced medical image data. In some embodiments, the enhanced medical image data may be integrated into an electronic healthcare record. Generating improved medical image reports based on the generated enhanced medical image data and the generated structured text data may include identifying and storing each finding indicated in the enhanced medical image data, correlating each finding to its corresponding structured text data, identifying corresponding portions for each finding in a radiology report, identifying discrepancies between the corresponding portions and the corresponding structured text data for each finding, and generating improved medical image reports by augmenting the radiology report with the identified discrepancies. The method may also include the step of presenting the generated improved medical image report to a physician for approval. The method may also include the step of presenting an alert to a physician in the case of an identified discrepancy.

Embodiments of the present disclosure may include a server system for generating improved medical image reports. The server system may be configured to receive medical images and textual data. Further, the server system may include an image processing unit configured to apply artificial intelligence computer vision techniques to the received medical images to generate enhanced medical image data, a text processing unit configured to apply natural language processing to the received textual data to generate structured text data, and a platform configured to generate an automated improved medical image report based on the generated enhanced medical image data and the structured text data.

Embodiments of the present disclosure may also include a system for generating improved medical image reports including a server system configured to receive medical images and textual data. The server system may include an image processing unit configured to apply an artificial intelligence computer vision techniques to the received medical images to generate enhanced medical image data, a text processing unit configured to apply natural language processing to the received textual data to generate structured text data, and a platform configured to generate an alert responsive to a detected discrepancy between the generated enhanced medical image data, the generated structured text data, and the received medical image and textual data.

Optionally, the artificial intelligence computer vision techniques may include a convolutional neural network. The server system may include a case manager configured to dispatch data and receive results from the image processing unit and the text processing unit. The server system may also include a platform configured to generate at least one of a clinical or non-clinical interface including the enhanced medical image data. The platform may be configured to incorporate the enhanced medical image data into an electronic healthcare record. In some embodiments, the natural language processing may include at least one recurrent neural network.

Embodiments of the present disclosure may also include a non-transitory computer-readable medium storing instructions that, when executed on one or more processors, cause the one or more processors to receive medical images, receive textual data, generate enhanced medical image data by applying an artificial intelligence module to the received medical images, generate structured text data by applying a natural language processing module to the received textual data, and generate improved medical image reports based on the generated enhanced medical image data and the generated structured text data.

Embodiments of the present disclosure may also include a non-transitory computer-readable medium storing instructions that, when executed on one or more processors, cause the one or more processors to receive medical images, receive textual data, generate enhanced medical image data by applying an artificial intelligence module to the received medical images, generate structured text data by applying a natural language processing module to the received textual data, and generate an alert based on a detected discrepancy between the generated enhanced medical image data, the generated structured text data, the received medical images and the received textual data.

Optionally, generating the enhanced medical image data may include applying a convolutional neural network. Further, applying a natural language processing module to the received textual data may include applying at least one recurrent neural network. The one or more processors may be configured to generate at least one of a clinical or non-clinical interface including the enhanced medical image data. Additionally, the one or more processors may be configured to incorporate the enhanced health-care related image data into an electronic healthcare record. In some embodiments, generating improved medical image reports based on the generated enhanced medical image data and the generated structured text data may include the one or more processors being configured to identify and store each finding indicated in the enhanced medical image data, correlate each finding to its corresponding structured text data, identify corresponding portions for each finding in a radiology report, identify discrepancies between the corresponding portions and the corresponding structured text data for each finding, and generate improved medical image reports by augmenting the radiology report with the identified discrepancies.

BRIEF DESCRIPTION OF DRAWING

Various embodiments of the present disclosure, together with further objects and advantages, may best be understood by reference to the following description taken in conjunction with the accompanying drawings, in the several figures of which like reference numerals identify like elements, and in which:

FIG. 3A illustrates a component (natural language processing servers) of the platform illustrated in FIG. 1 in a first state (training), according to some embodiments of the present disclosure.

FIG. 3B illustrates a component (natural language processing servers) of the platform illustrated in FIG. 1 in a second state (application), according to some embodiments of the present disclosure.

FIG. 8 illustrates an aspect of a graphical user interface in accordance with an embodiment of the present disclosure.

FIG. 9 illustrates an aspect of a graphical user interface in accordance with an embodiment of the present disclosure.

DETAILED DESCRIPTION

The present disclosure is related to systems and methods for the improved analysis and generation of medical imaging reports. In particular, embodiments of the present disclosure may include receiving medical images and textual data and generating improved medical imaging reports by applying artificial intelligence and natural language processing techniques. For example, medical images may include images from medical image archives and scanning devices such as magnetic resonance imaging (MRI), computed tomography (CT), X-Rays and the like. Additionally, textual data may include radiological reports, electronic health records, referring letters, and the like.

Figure 1:
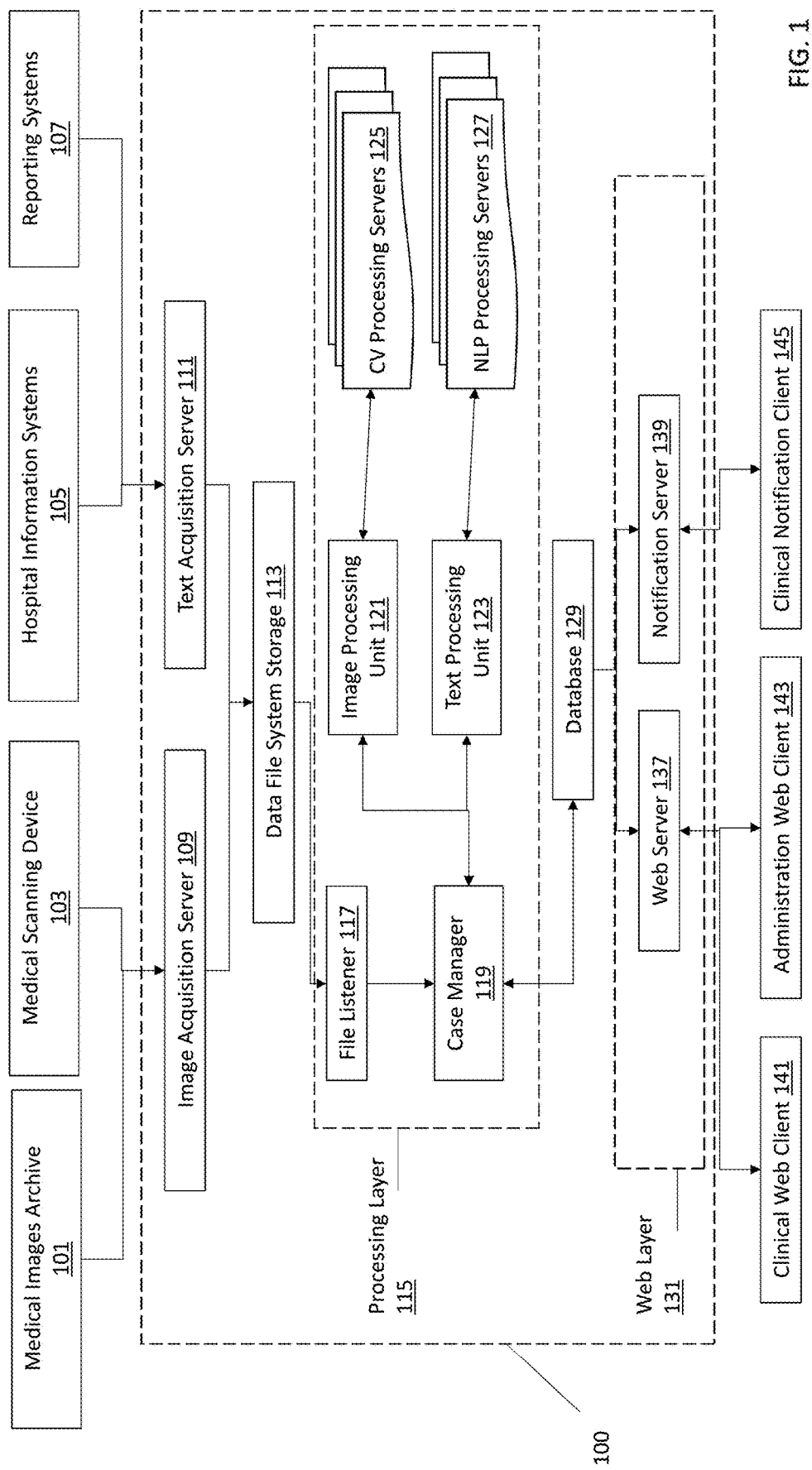
FIG. 1 illustrates a platform built in accordance with an embodiment of the present disclosure.

FIG. 1 illustrates a platform built in accordance with the disclosed systems and methods. As illustrated in FIG. 1, a platform 100 may be configured to receive medical images and textual data. For example, the platform 100 may be communicatively coupled to a medical images archive 101 and/or medical scanning device 103 so as to receive medical images. Medical images archive 101 may include a picture archiving and communication system (PACS) server and the like. In some embodiments, the medical images archive 101 may be integrated into an information technology (IT) system within a hospital environment that is configured to collect, store, and distribute imaging studies between scanning devices, and workstations in a clinical environment. A medical scanning device 103 may include radiological equipment such as a CT, MRI, and the like. Medical images received by the platform 100 may be received using the Digital Imaging and Communications in Medicine (DICOM) format and the like.

Further, the platform 100 may be configured to receive textual data by way of being communicatively coupled to hospital information systems 105 and/or reporting systems 107. The hospital information systems 105 and/or reporting systems 107 may provide radiological reports, radiology diagnosis, electronic health records, referring letters, related metadata, information containing medical text statements, and the like. In some embodiments, the textual data may be received using DICOM, SR, Health Level 7 (HL7) protocol, JavaScript Object Notation (JSON), eXtensible Markup Language (XML) formats, using application programming interfaces and the like. In some embodiments, the hospital information system 105 may be integrated into an IT system in a hospital that is configured to manage medical records including radiology reports. Such a system may be configured to distribute messages in HL7 format and the like. In some embodiments, the reporting systems 107 may include dedicated software configured to write radiology reports. The reporting systems 107 may be capable of distributing reports through HL7 protocol and/or application programming interface (API) calls.

Medical images and data may be received by an image acquisition server 109 integrated into the platform 100 and configured to receive medical images and data from the medical images archive 101 and/or medical scanning device 103 as single DICOM messages. The image acquisition server 109 may include a DICOM listener component and be configured to filter irrelevant imaging studies and/or series, and identify images associated with a certain imaging series and/or imaging study. For example, a region of interest may include a package of tens to thousands of images, and the image acquisition server 109 may receive the package of images, filter and clean the images, and determine regarding their association to a certain imaging series and/or imaging study. For example, the image acquisition server 109 may look at the metadata and description to filter out a series of images not relevant for analysis by the platform 100.

Similarly, textual data from hospital information systems 105 and/or reporting systems 107 may be received by a text acquisition server 111 also integrated into the platform 100. The text acquisition server 111 may include a HL7 listener component and be configured to filter irrelevant messages and save reports to a file system. For example, the text acquisition server 111 may review text related to radiology reports and attach a unique identifier (e.g., accession number) to any received text.

Medical images and textual data may then be transmitted from the image acquisition server 109 and text acquisition server 111 to the data file system storage 113. Image data processed by the image acquisition server 109 and/or textual data processed by the text acquisition server 111 may be stored in a data file system storage 113. Corresponding image data and textual data may be linked and stored in the data file system storage 113. Further, the stored data may be sorted in dedicated sub-folders in accordance with their processing status.

The platform 100 may include a processing layer 115 configured to access the data (e.g., medical image data and textual data) stored in the data file system storage 113. In some embodiments, the processing layer 115 may include a file listener 117, a case manager 119, an image processing unit 121 and related computer vision (CV) servers 125, and a text processing unit 123 and related natural language processing (NLP) servers 127. The file listener 117 of the processing layer 115 may be configured to detect new imaging studies and related textual data being stored in the data file system storage 113. The file listener 117 may be configured to finalize the receipt of new files and manage the queue and/or order in which new files are processed.

The file listener 117 may work in conjunction with the case manager 119. The case manager 119 may gather all the data (including medical images and textual data) related to a single imaging study (e.g., associated with a single unique identifier or accession number) and route it to appropriate processing units (e.g., image processing unit 121, text processing unit 123). The case manager 119 may route data based on its associated metadata. The case manager 119 may also receive processed data from the image processing unit 121 and text processing unit 123 and compare and combine results, generate updated findings, and update a database 129.

Medical image data may be received by the image processing unit 121 of the processing layer 115 of platform 100. The image processing unit 121 may be configured to analyze the medical image data to perform computer image processing, and utilize one or more computer vision servers configured with artificial intelligence components to automatically detect findings, areas of interest, provide measurements, and other characteristics. Detected findings may include abnormalities, suspected areas as well as other areas of clinical interest, including for example, tumors, lesions, nodules, opacities, irregular blood vessels, blood clots and the like. The image processing unit 121 may be configured to automatically identify suspected abnormalities, their location and other characteristics.

In some embodiments, the image processing unit 121 may apply one or more artificial intelligence based algorithms embodied on one or more computer vision (CV) servers 125 to the received medical image data to generate enhanced medical image data, which may also be referred to as automatic imaging detection results. The generated enhanced medical image data may include findings detected by the image processing unit 121.

More particularly, the image processing unit 121 may dispatch images to one or more computer vision (CV) servers 125 configured to run convolutional neural networks (CNN) or other computer vision techniques. Images may be dispatched by the image processing unit 121 to the appropriate computer vision (CV) server 125 based on their modality (e.g., CT, MRI) and body region (e.g., chest, brain). Prior to applying convolutional neural networks by way of the CV server 125, the image processing unit 121 may preprocess the image data. Examples of preprocessing image data include normalizing the pixel information in the image data, the size of voxels, and/or the size of the data provided. Further, preprocessing image data may include segmenting different images. The image processing unit 121 may also post process results from the convolutional neural network algorithms. In particular, post processing steps may include undoing normalizations to return images to normal sizes. Post processing may also include data cleaning, adjacent component/morphology analysis, and contour operations.

The computer vision (CV) servers 125 may include one or more separate convolutional neural networks. For example, a regression convolutional neural network may be used to estimate parameters such as the centroid coordinates of a pulmonary nodule. Regression convolutional neural networks may be used to create a region of interest for an image. A regression convolutional neural network may be configured to receive an image having a pre-defined size and output a vector of estimated parameters corresponding to a region of interest.

Additionally, computer vision (CV) servers 125 may include a semantic segmentation convolutional neural network. A semantic segmentation convolutional network may be configured to associate each pixel of an image with a class label. A semantic segmentation convolutional neural network may be used to measure lesions in organs. The semantic segmentation convolutional neural networks may utilize pyramid scene parsing and dilated convolutions. In some embodiments, the semantic segmentation convolutional network may be configured to receive an image of any size and output an image of the same size as the input with masks of segmentations.

Additionally, the computer vision (CV) servers 125 may include classification convolutional neural networks that are configured to classify images on a global and/or local level. Examples of global level classifications may include determining whether an image is a CT image, MRI image and the like. Examples of local level classifications may include a classification as to whether a region of interest includes a benign and/or cancerous lesions. In some embodiments, the classification convolutional neural networks may be configured to receive an image with a pre-defined size and output a vector with a field corresponding to each possible classification. Each value in the vector may correspond to a score for the given class. Higher values may be associated with a predicted class.

In some embodiments, the computer vision (CV) servers 125 may work in unison to provide image processing. For example, to measure the ascending and descending aortic caliber, a classification convolutional neural network may be used to classify (and determine) CT slices that contain a thoracic aorta. Further, a regression convolutional neural network may be applied to estimate the center of the thoracic aorta. And still further, a semantic convolutional neural network may be used to determine the diameter of the thoracic aorta.

Outputs of the computer vision servers 125 may be passed to the image processing unit 121. The image processing unit 121 may then generate enhanced medical image data that includes information related to whether an area of interest was located, the characteristics of the area of interest, and the location of the area of interest within the received medical images.

As discussed above, the image processing unit 121 may include an artificial intelligence component 207 embodied within computer vision (CV) servers 125 configured to generate enhanced medical image data 211 when provided with medical image data 209. FIG. 2A illustrates the training stage 201 of the artificial intelligence component 207 of the image processing unit 121 and related computer vision (CV) servers 125 of FIG. 1.

As discussed above, in some embodiments, the artificial intelligence unit 207 may include one or more multi-layer convolutional neural networks (e.g., computer vision servers 125). Each of the multi-layer convolutional neural networks may be trained upon radiologist marked data.

For example, training data may include global annotations related to the entire CT scan (e.g., CT scan does or does not contain liver lesions). Training data may also include global annotations related to CT scan slices (e.g., CT scan slice does or does not contain liver lesions, CT scan slice does or does not contain liver). Training data may also include locations of findings (e.g., x, y, z coordinates of centroid pulmonary nodule). Training data may also include 2D segmentation of organs and findings/areas of interest. Training data may also include 3D segmentation of organs and findings/areas of interest.

In some embodiments, the artificial intelligence unit 207 may include one or more convolutional networks configured for lesion detection and measurement. The convolutional network configured for lesion detection and measurement may be trained on annotated slices (e.g., slice does or does not consist of relevant organ). The convolutional neural network may also be trained on slices having the contour of the relevant organ annotated. Further, the convolutional neural network may be trained on slices having the contour of any relevant lesion annotated.

In some embodiments, the artificial intelligence unit 207 may include networks trained to measure thoracic aortas. In such an embodiment, the networks may be trained on annotated CT scans. Annotated CT scans may include information regarding whether a particular CT scan slice is or is not suitable for thoracic aorta measurement. For those slices suitable for thoracic aorta measurement, the annotated CT scans may also indicate the x and y coordinates of the ascending and descending aortas. Slices suitable for thoracic aorta measurement may also have the 2D contour of ascending and descending aortas annotated.

Figure 2B:
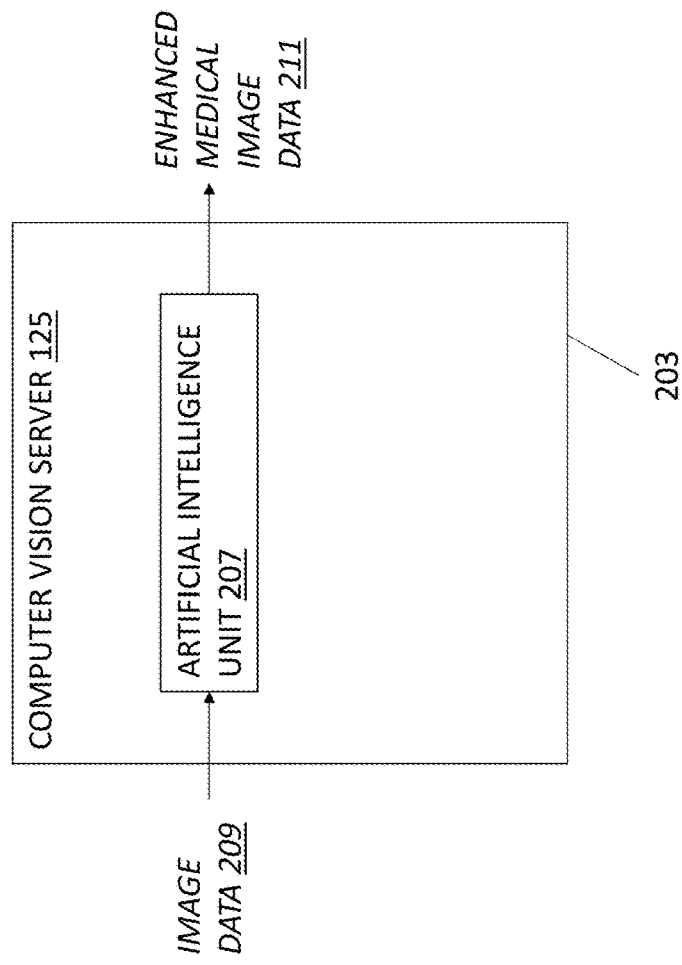
FIG. 2B illustrates a component (computer vision processing servers) of the platform illustrated in FIG. 1 in a second state (application), according to some embodiments of the present disclosure.
Figure 2A:
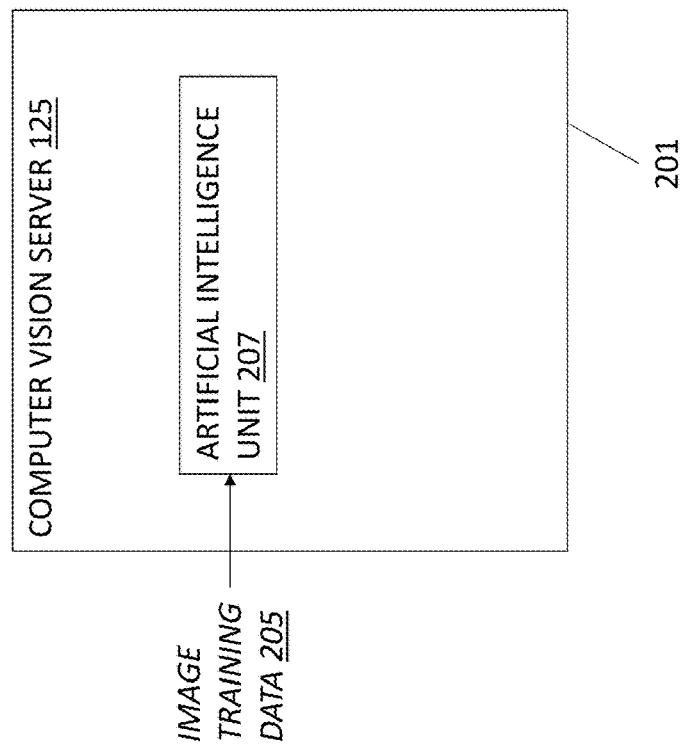
FIG. 2A illustrates a component (computer vision processing servers) of the platform illustrated in FIG. 1 in a first state (training).

Once the artificial intelligence unit 207 of the computer vision (CV) servers 125 are trained, the image processing unit 121 of FIG. 1 may be applied or operated as illustrated in FIG. 2B. In particular, image data 209 may be received by the image processing unit 121 and the artificial intelligence unit 207 of computer vision servers 125 may apply the trained algorithm(s) to the received image data 209 to produce enhanced medical image data 211.

Turning back to FIG. 1, the case manager 119 may dispatch textual data to the text processing unit 123 of the platform 100. In some embodiments, the text processing unit 123 may be configured to communicate with one or more natural language processing (NLP) servers 127 configured to apply the natural language processing algorithms to the received textual data in order to generate structured text data.

In some embodiments the NLP servers 127 may include one or more recurrent neural networks. The text processing unit 123 may preprocess the textual data. For example, a radiology report may be parsed into sentences and/or sections (e.g., title, sentences), and then each section may be routed to the relevant NLP server 127. Further, the text processing unit 123 may be configured to receive the output from each of the NLP servers 127 and postprocess the results from the NLP servers 127 by reconstructing the radiology report with the output from the NLP servers 127.

In some embodiments, the NLP servers 127 may include classification recurrent neural networks (RNNs). The classification RNNs may be configured to classify text into specific classes on a global and/or local level. Examples of global classifications include determining that a report does or does not contain mention of liver lesions. Examples of local classifications includes that a sentence does or does not contain mention of liver lesions. In some embodiments, the classification RNNs may use layered bidirectional long short-term memory (LSTM) architecture.

In some embodiments, the NLP servers 127 may include RNNs configured to provide sentiment analysis. In particular, the RNNs may be configured to classify text as having positive or negative sentiment. For example, the RNNs may indicate whether the radiologists positively or negatively reported liver lesions in the radiology report.

In some embodiments, a series of NLP servers 127 running various algorithms may be used. For example, a radiology report may be first parsed into sentences. Sentences containing words from a pre-defined set may be identified as "suspicious sentences." The suspicious sentences may then be passed to a NLP server 127 configured to apply a bi-directional LSTM classification neural network. The bi-directional LSTM classification neural network may be configured to classify between sentences that mention a finding and sentences that do not mention a finding. The bi-directional LSTM classification neural network may be configured to output a list of sentences that mention the finding.

The list of sentences that mention the finding may then be passed to a second NLP server 127 configured to apply a bi-directional LSTM classification neural network that is configured for sentiment analysis. This network may be configured to classify between sentences that mention the findings positively and those sentences that mention the findings negatively. This network may be configured to output a list of sentences that mention the finding positively.

As illustrated in FIGS. 3A-3B, the natural language processing (NLP) servers 127 of FIG. 1 may include a natural language processing module 307 that operates in a training stage 301 (see FIG. 3A) and an operational or application stage 303 (see FIG. 3B).

The text processing unit 123 may be configured to receive a radiology report related to a particular identifier (e.g., accession number) from the case manager 119, and may be configured to route radiology reports to relevant NLP servers 127 based on their modality (e.g., CT, MRI) and body region (e.g., chest, brain).

During a training stage 301, the natural language processing module 307 may be trained in two stages. In a first stage, the natural language processing module 307 may create a vocabulary for each type of textual data (e.g., tweets, emails, radiology reports, metadata). In a second stage, the natural processing module 307 may be trained based on textual data including annotations. In some embodiments, the natural language processing module 307 may apply sentiment analysis. In some embodiments, the natural language processing algorithm may be built after analyzing radiology reports and constructing a medical vocabulary data set. In some embodiments, the natural language processing module 307 may include natural language processing deep learning classifiers based on a radiological vocabulary.

For example, during the training stage 301, the natural language processing module 307 may construct a dictionary of "suspicious" words or phrases. This may be a list of words or phrases that are defined by a radiologist as being used to report a specific finding. Then, in a next step, sentences that include the suspicious words or phrases may be extracted from a training set of thousands of radiology reports. The extracted sentences may be annotated based on whether they don't mention, positively mention, or negatively mention the finding. The natural processing module 307 may then be trained based on the annotated extracted sentences.

Further, during an operational stage 303, a trained natural language processing module 307 may be applied to the received textual data 309 in order to generate structured text data 311. The generated structured text data 311 may include stratified, categorized and annotated statements regarding patient procedures and conditions.

Textual data 309 received by the text processing unit 123 may include structured and unstructured text statements associated with a patient and/or imaging procedure. For example, textual data 309 may include radiology reports of analyzed images, prior radiology reports, referring physician letters and the like. Textual data 309 may also include metadata related to patient and/or image procedures. For example, metadata may include DICOM and/or HL7 tags that contain information regarding patient age, referring unit, procedure name, imaging protocol, modality type and other details.

Referring back to FIG. 1, the enhanced medical image data produced by the image processing unit 121 and the structured text data produced by the text processing unit 123 may be transmitted to and received by the case manager 119. As discussed previously, the case manager 119 may then store the enhanced medical image data and structured text data in a relational database 129. The relational database 129 may be configured to store and handle all data related to incoming imaging studies, radiology reports, processing results, processing status, and detected findings. In some embodiments, the database 129 may serve as the output of the processing layer 115. Further, in some embodiments, the database 129 may serve as the input for the web layer 131.

Further, the case manager 119 may be configured to perform a comparative analysis between the enhanced medical image data and the structured text data. In some embodiments, the comparative analysis may involve cataloguing each finding indicated in the enhanced medical image data and correlating it to information derived from the structured text data. The findings may be stored in the database 129.

The web layer 131 may include a web server 137 and notification server 139.

The web server 137 may be configured to manage users, reading groups, clinical and administrative requests. Further, the web server 127 may be configured to query the database 129 for studies and findings and push notifications to subscribers based on links between the reports and users in the system.

For example, the web server 137 may be communicatively coupled to a clinical web client 141 and an administration web client 143. The clinical web client 141 may be configured to present a worklist of unreported findings for a certain user and/or reading group. The clinical web client 141 may include a graphical user interface that allows the visualization of different findings. The clinical web client 141 may allow for the filtering and sorting of findings, presenting key images and relevant sections from radiology reports, and allowing the management of various reviewing statuses per each detected finding.

The administrative web client 143 may include a user interface configured for use by a system administrator for supporting a clinical team. The administration web client 143 may allow the presentation of processing status of the system, viewing a list of received studies and their processing status, managing users in the system, changing system configuration and controlling activation of the processing layer.

As discussed above, the web layer 131 may also include a notification server 139. The notification server 139 may be configured to manage subscriptions for notifications from workstations used by clinical users. For example, the notification server 139 may be configured to listen to the database for new studies and findings and push notifications to subscribers based on links between reports and users in the system.

The notification server 139 may be configured to provide notifications via a clinical notification client 145. The clinical notification client 145 may be configured as a component in workstations in a clinical environment (e.g., radiology department). In some embodiments, the clinical notification client 145 may provide an active user (e.g., radiologist) with on-screen real time notifications on new unreported findings. Notifications may include direct hyperlinks to viewing the finding in the clinical web client 141 for quick evaluation immediately after writing the report by the radiologist.

Using the information stored in database 129 the platform 100 may be capable of generating automated radiology reports for each finding in the enhanced medical image data set. Further, the platform 100 may receive radiology reports generated by a radiologist. In some embodiments, the platform 100 may compare the automated radiology reports with the radiology reports generated by a radiologist in order to identify discrepancies. Discrepancies may include conditions and findings that were unreported in the radiology reports generated by a radiologist, as well as errors in the radiology reports related to findings.

In other embodiments, a detected discrepancy may trigger the generation of an alert. The alert may then be displayed on a radiologists' computer screen. The radiologist may then view the radiologist report and one or more notations indicating discrepancies between the computer generated report and the originally determined radiologist report.

Radiologist reports may include information regarding the type of exam including the date, time, and type of imaging study, clinical history, comparison, technique, findings, and impression. Radiologist reports may be referred to as textual data.

In some embodiments, the platform 100 may be configured to generate a list of items for which there is a high probability of uncorrelated, unreported or misreported medical findings or conditions, noting a discrepancy between the radiologist's interpretation and the automated radiology reports. These reports may be published by the components of the web layer 131 and provided to the appropriate client: clinical web client 141, administration web client 143, and/or the clinical notification client 145.

The platform 100 may be configured to generate a clinical graphical user interface configured for display to a clinician (e.g., clinical web client 141, clinical notification client 145). The platform may also be configured to generate a non-clinical graphical user interface (e.g., administration web client 143).

The clinical graphical user interface may be provided to a physician, radiologist, hospital administration, nursing staff, and the like. The clinical interface may provide a user with a list of discrepancies identified between the automated radiology report and the radiology report generated by a physician. In some embodiments, the clinical graphical user interface may be configured to display a copy of the medical image with areas of interest highlighted, along with the original radiology report generated by the physician supplemented by the automated radiology report generated by the systems discussed herein. Additionally, in some embodiments, agreement/disagreement between the automated radiology report and the physician generated original radiologist report may be displayed. For example, in some embodiments, agreement between the radiology report and the automatic image analysis may be presented in green to a user. Additionally, negative reporting of features of interest (e.g., pulmonary nodules) may be presented in red. For example, the system will present the user with a list of items and areas of interest where there is a probability of uncorrelated, unreported or misreported medical findings or conditions, noting a discrepancy between the human physician interpretation and the automatic image detection.

The non-clinical graphical user interface may be provided by a non-clinical interface to a hospital administrator and the like. The non-clinical graphical user interface may show common trends, stratification and the like. In particular, the non-clinical graphical user interface may allow for the grouping of medical images by condition, findings, protocols, demographic information, discovered conditions and the like.

Figure 4:
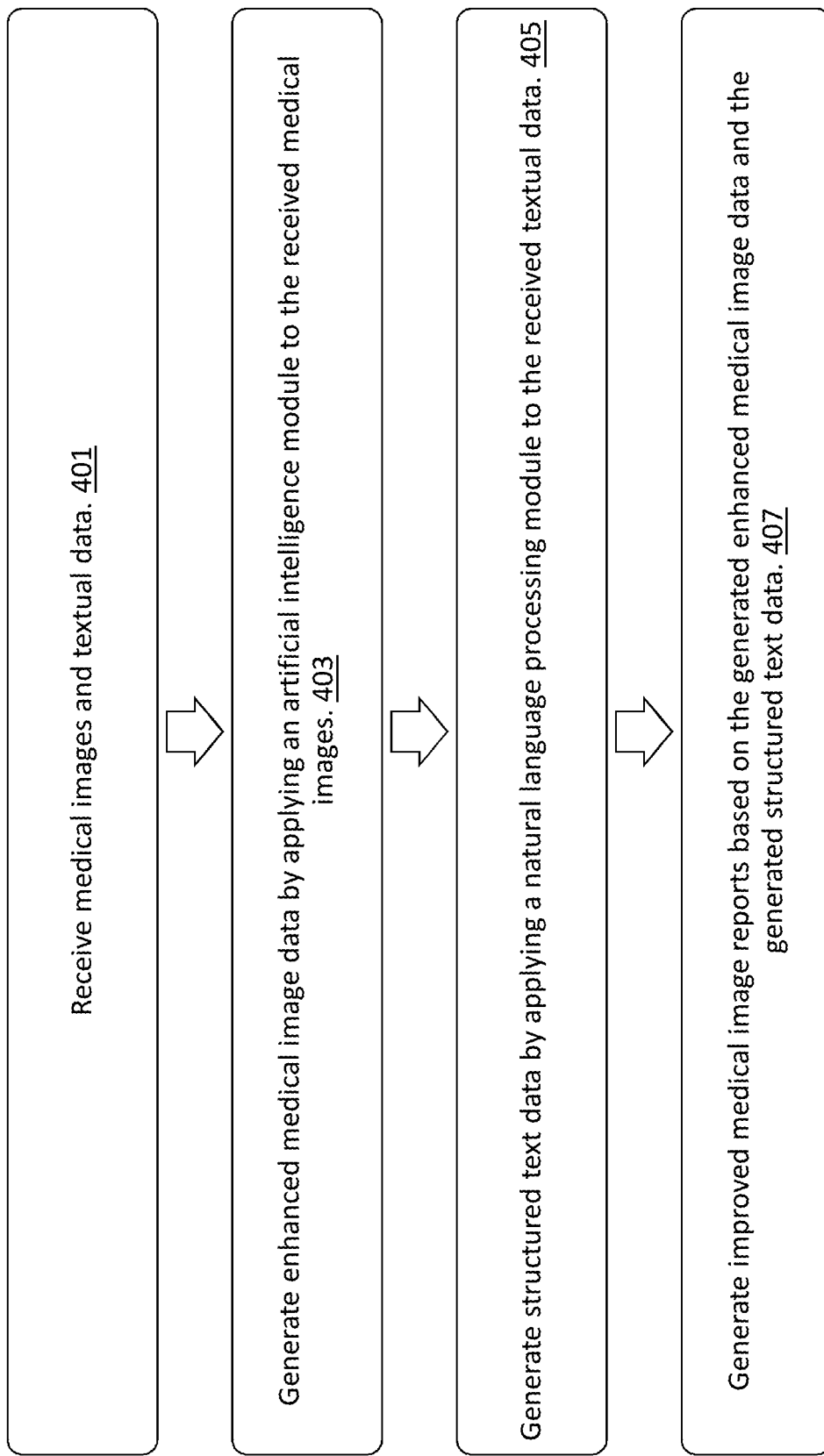
FIG. 4 illustrates a method in accordance with an embodiment of the present disclosure.

FIG. 4 illustrates a method in accordance with embodiments of the present disclosure. The method may include the steps of receiving medical images and textual data 401, generating enhanced medical image data by applying an artificial intelligence module to the received medical images 403, generating structured text data by applying a natural language processing module to the received textual data 405, and generating improved medical image reports based on the generated enhanced medical image data and the generated structured text data 407.

Further, in some embodiments, generating improved medical image reports based on the generated enhanced medical image data and the generated structured text data may include identifying and storing each finding indicated in the enhanced medical image data, correlating each finding to its corresponding structured text data, identifying corresponding portions for each finding in a radiology report, identifying discrepancies between the corresponding portions and the corresponding structured text data for each finding, and generating improved medical image reports by augmenting the radiology report with the identified discrepancies.

As discussed, the disclosed methods may include the processing of textual data using various text analysis and language processing algorithms to create a stratified, categorized and annotated list of statements regarding the patient and procedure. Further, a comparative analysis may be performed between the medical text statements derived by the platform and the detections in the radiology report. In some embodiments, the systems and methods may present a user with a list of items and areas of interest where there is a probability of uncorrelated, unreported or misreported medical findings or conditions, noting a discrepancy between the human physician interpretation and the automatic image detection. Thus, the disclosed systems and methods may be able to catch discrepancies and possible missed details that could reduce diagnostic errors, misreporting and misdiagnosis rates. The system can also detect findings which were not requested as part of the referring clinical question (referred to as Incidental findings or Incidentalomas).

Figure 5:
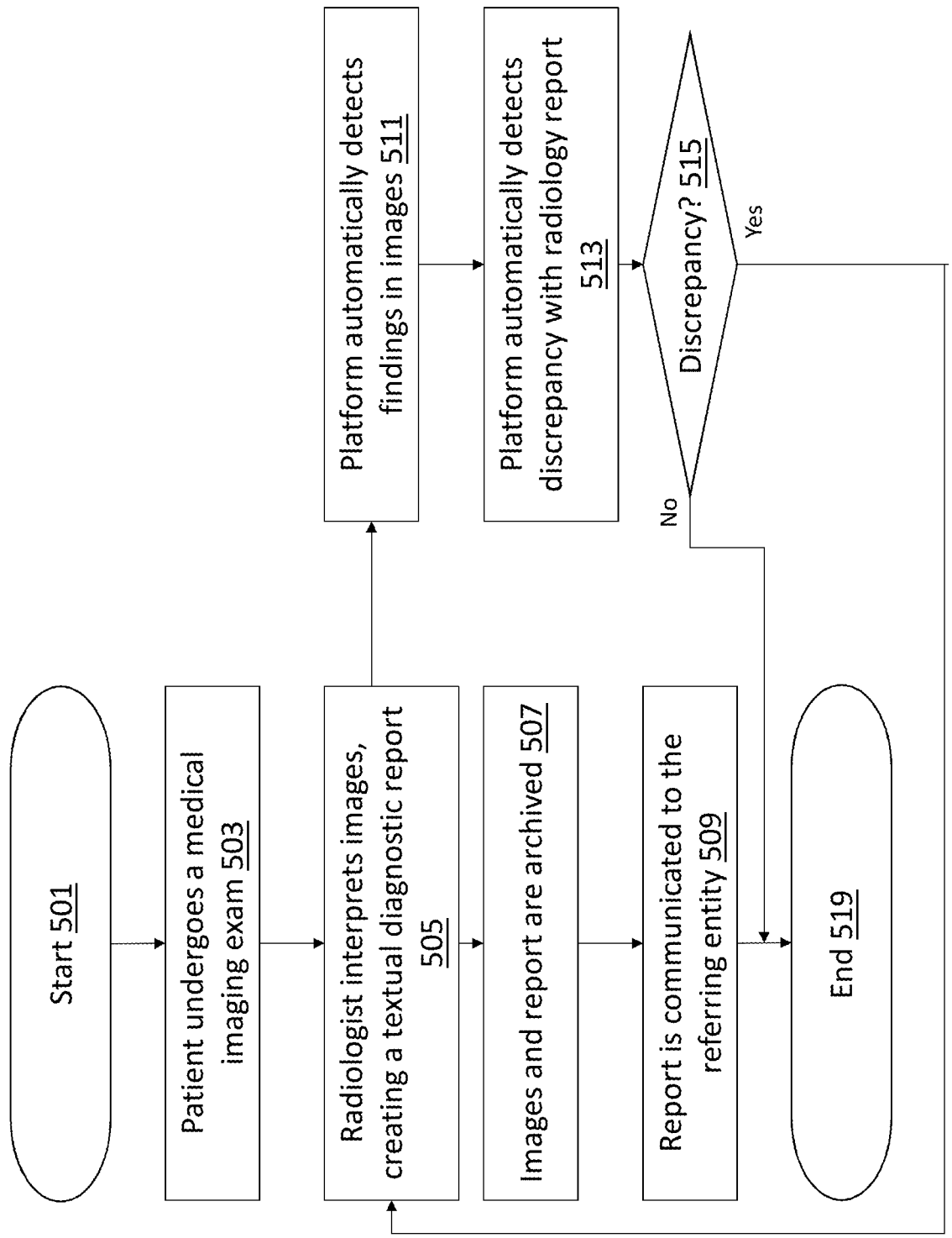
FIG. 5 illustrates a flow diagram illustrating the operation of a platform built in accordance with an embodiment of the present disclosure.

FIG. 5 provides a flowchart illustrating the operation of a platform built in accordance with the embodiments discussed herein in a clinical setting. As illustrated, in some embodiments, the workflow may start 501 when a patient undergoes a medical imaging exam 503. Examples of medical imaging exams 503 include CT scans, X-rays, MRI, and the like. In a next step 505, a radiologist or trained physician may interpret the medical imaging exam and create a textual diagnostic report. After the images are interpreted and a textual diagnostic report is created, the images and reports may be archived in a database 507 and the report may be communicated to a referring entity or physician 509. In accordance with the disclosed embodiments, the platform may also be provided with a copy of the radiologists' textual diagnostic report and be configured to automatically detect findings in the images 511. The platform may be further configured to automatically detect any discrepancies between the automatically detected findings and the radiology report 513. In the event a discrepancy 515 is not found, the process may come to an end 519. However, if a discrepancy is found, the platform may provide the radiologist with a summary of the discrepancy. Accordingly, a radiologist may then correct or edit the originally provided radiology report.

In the illustrated operation, image processing and detection of findings may be initiated as soon as a medical image is obtained. Further, the radiology report may be automatically scanned using the natural language processing elements discussed above.

Figure 6:
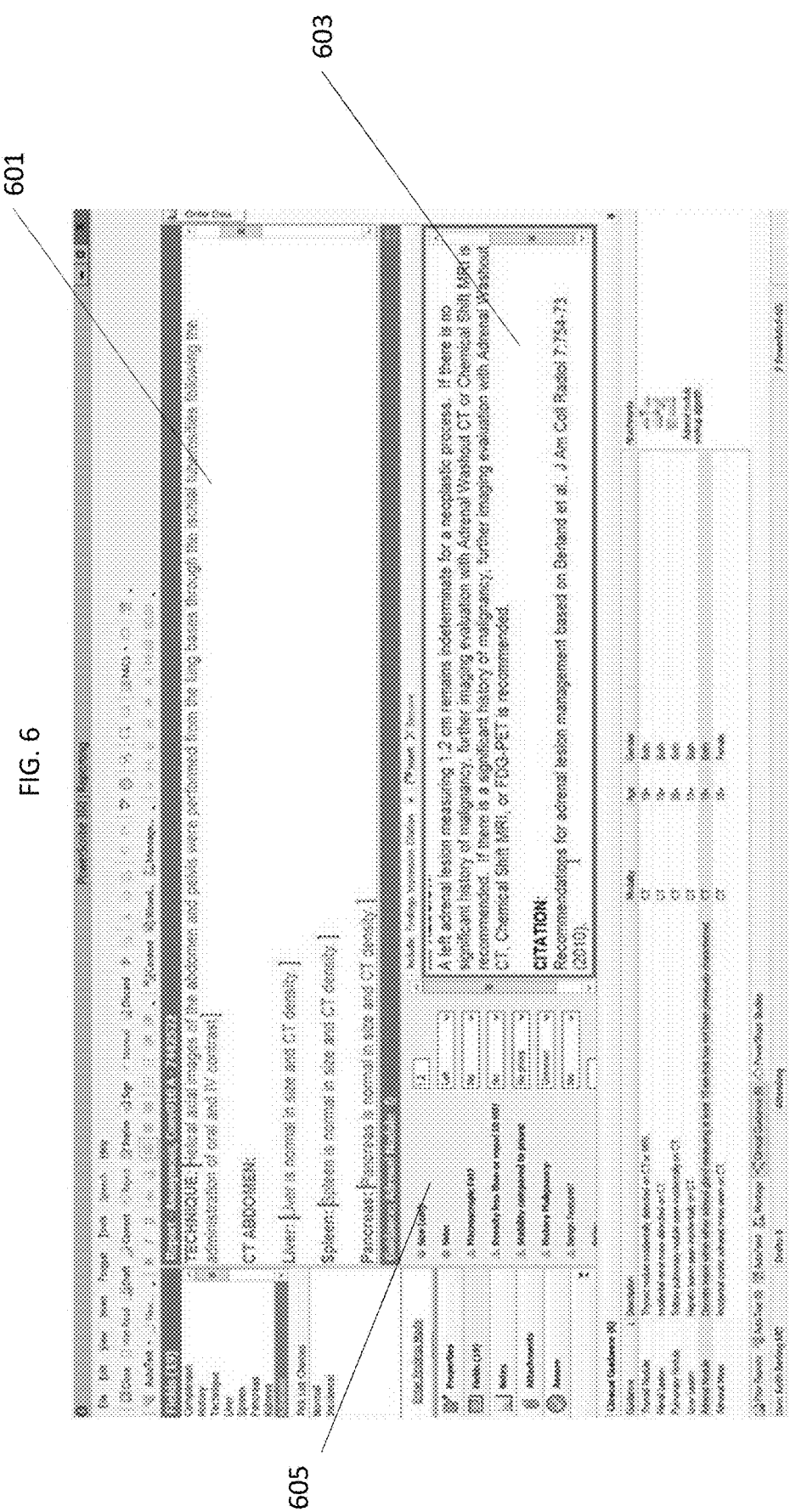
FIG. 6 illustrates an aspect of a graphical user interface in accordance with an embodiment of the present disclosure.

FIG. 6 illustrates a graphical user interface in accordance with an embodiment of the present disclosure configured to be displayed to a physician and/or radiologist. In particular, the radiology report generated by a radiologist may be displayed in a first panel 601 of a graphical user interface. A second panel 603 may be configured to display the structured text automatically generated by the platform described herein. Further, a third panel 605 may be configured to display information regarding the size and/or location of the findings. Accordingly, as illustrated in FIG. 6, the platform's automatically generated structured text may be incorporated into a graphical user interface that is configured for radiology notes and/or reporting on radiological images.

Figure 7:
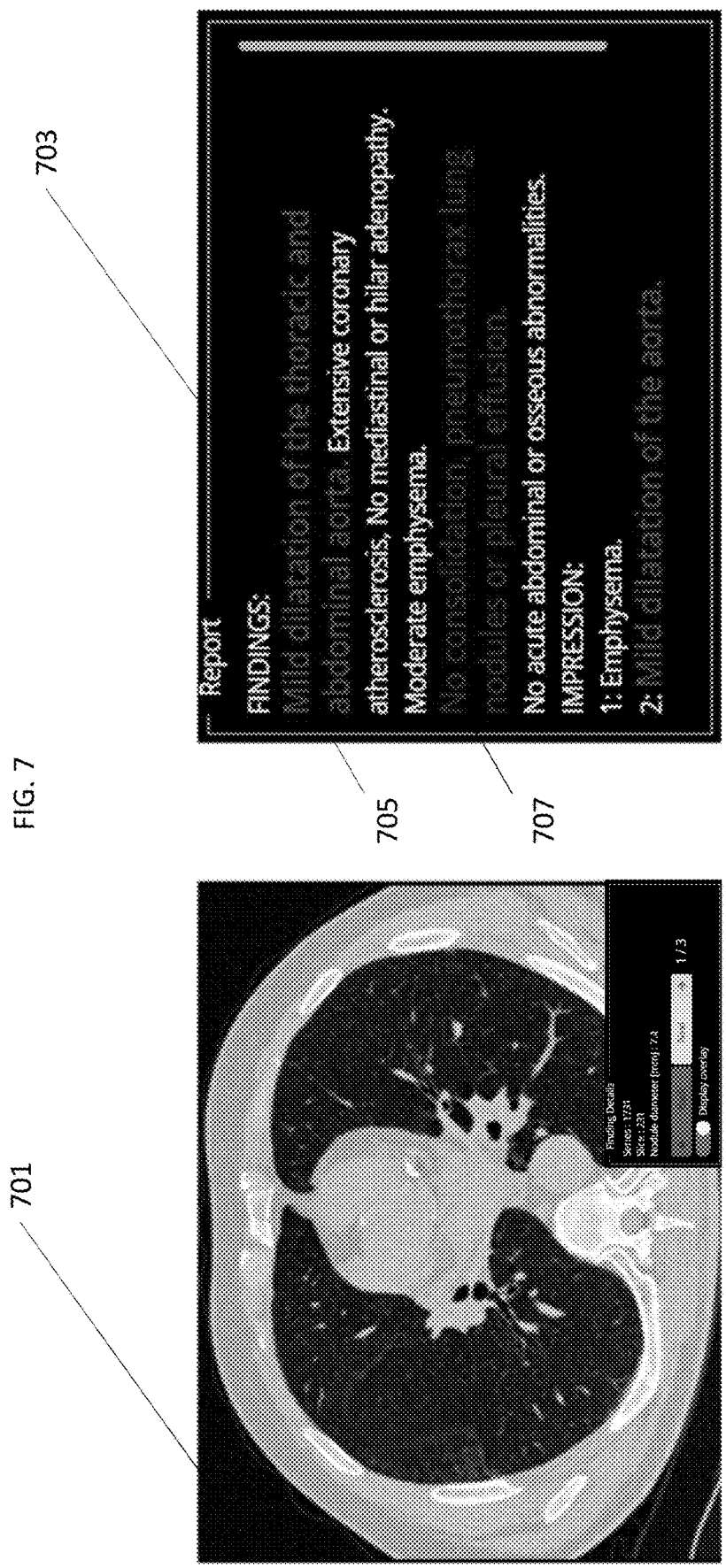
FIG. 7 illustrates an aspect of a graphical user interface in accordance with an embodiment of the present disclosure.

FIGS. 7 and 8 illustrate aspects of a graphical user interface in accordance with an embodiment of the present disclosure. As illustrated in FIG. 7, the graphical user interface may display a medical image (e.g., slice/s from chest CT scan) in a first panel 701. As illustrated, the medical image may be augmented with highlighting and other markers that indicate regions of interest as determined by the image processing unit. A second panel 703 may display an augmented report. In particular, additional information generated by the structured text and platform may be integrated into the report 705. Further, discrepancies between the structured text and platform may also be integrated into the report 707. In some embodiments, additional information 705 and discrepancies 707 may be color-coded when displayed. Similarly, positive and negative findings may be color-coded when displayed.

Similarly, FIG. 8 illustrates a medical image (e.g., slice/s from abdomen CT scan) in a first panel 801. A second panel 803 may display an augmented report. In particular, additional information and/or positive/negative findings generated by the structured text and platform may be integrated into the report 805. Further, discrepancies between the structured text and platform may also be integrated into the report 807.

FIG. 9 illustrates an aspect of a graphical user interface in accordance with an embodiment of the present disclosure. As discussed above, in some embodiments, a platform such as platform 100 (and more particularly, the result processing unit 123) may be configured to generate a list of items for which there is a high probability of uncorrelated, unreported or misreported medical findings or conditions, noting a discrepancy between the radiologist's interpretation and the automated radiology reports. FIG. 9 illustrates such a list.

As illustrated in FIG. 9, in some embodiments aggregated information from several or all analyzed cases and procedures may be displayed. Accordingly, the graphical user interface may be used to analyze common trends, and allow for the stratification and categorization of information into groups and graphs summarizing the information. For example, similar conditions, similar findings, cases categorized by protocols, categorized by demographic information, categorized by discovered conditions, and the like.

In an alternative embodiment, the disclosed platform may be used to automatically check the quality and accuracy of every radiological exam and interpretation occurring in a hospital or similar institution.

As discussed above, in some embodiments, the disclosed systems and methods may be integrated into a picture archiving and communication system (PACS) server. A PACS server may be configured for the digital storage, transmission, and retrieval of radiology images. PACS servers may include both software and hardware components and may be configured to directly interface with and/or acquire digital image with imaging modalities. Medical images may be stored and transferred in the PACS system using the standardized, universal format DICOM (Digital Imaging and Communications in Medicine). Further, the PACS server may be configured to transfer images to a workstation for viewing and reporting. Accordingly, a PACS viewer may be communicatively coupled to the PACS server, and include a software that is installed on a corresponding workstation in order to receive and display radiology images. Radiology images may be archived into storage or a database for retrieval at a later time. The storage or database may be communicatively coupled to the PACS server and the PACS system may be configured to manage the storage of these radiology images. In some medical environments, PACS may provide the electronic platform for radiology images interfacing with other medical automation systems such as Hospital Information System (HIS), Electronic Medical Record (EMR), Practice Management Software, and Radiology Information System (RIS). Accordingly, the disclosed systems and methods may be used to improve the functionality of PACS system.

In some embodiments, the described systems and methods may be applied to medical images of cancer and/or cardiovascular indications. Additional examples of applications of the platform include thoracic aortic dilatation detection, pulmonary nodule detection, abdominal aortic dilatation detection, liver lesion detection and the like. Further examples of illnesses and disease that may be early detected with the disclosed systems and methods include (but are not limited to) liver lesions, pancreatic lesions, renal lesions, adrenal lesions, pulmonary nodules, mediastinal lesions, lymph nodes, thoracic aortic dilatation, abdominal aortic dilatation, pulmonary artery dilatation, pulmonary embolism and the like.

In some embodiments, a computer vision deep-learning algorithm may be used to analyze medical images. Further in some embodiments, natural language processing deep-language algorithms may be used to analyze textual radiology reports, which may correspond to the medical images. The application of these techniques may be useful in the early detection of disease states including cancer.

The application of the techniques discussed herein may allow for the detection of formerly missing actionable findings, alert a physician and help physicians provide a more comprehensive diagnosis for the patient.

As opposed to conventional systems that may rely upon computer vision, the disclosed systems may also utilize natural language processing on related patient notes and the electronic health record.

In some embodiments, the disclosed systems and methods may be integrated into the backend server, thereby the disclosed systems and methods may not require the adoption of independent server systems. In contrast, conventional systems rely on doctor initiation and/or a specific protocol.

Further, while in conventional systems, most of the findings reported are false positives or not significant, the disclosed systems are able to utilize information regarding the clinical context and patient history (by way of the electronic health record) and report only on significant findings. Accordingly, user fatigue is reduced, and the provided systems increase the efficiency of providing radiologist reports on medical imagery.

The disclosed systems and methods provide benefits to patients, radiologists, and/or hospital systems. For example, benefits provided to patients may include higher detection rates on broader areas of pathologies, increased number of patients that go to needed follow up care (screening, consultation), the promotion of early, efficient and cheaper care, especially when detecting small cancer onsets, better outcomes (e.g., morbidity/mortality) due to early detection, detection of pre-cancerous/cardiovascular indications that are often missed and asymptomatic (e.g., lesions, masses, tumors, nodules, ectasia, aneurysm, etc.).

Radiologists and the hospital system may also be provided with additional benefits. For example, benefits provided to radiologists and the hospital system may include increased detection rates, quality and coverage of the interpretation, and decreased chances of diagnostic error. Further, the disclosed systems and methods can be integrated into existing computing systems, accordingly, the physician workflow is not impacted.

As used herein, the term "module" may be understood to refer to computer executable software, firmware, hardware, or various combinations thereof. It is noted that the modules are exemplary. The modules may be combined, integrated, separated, or duplicated to support various applications. Also, a function described herein as being performed at a particular module may be performed at one or more other modules and by one or more other devices instead of or in addition to the function performed at the particular module. Further, the modules may be implemented across multiple devices or other components local or remote to one another. Additionally, the modules may be moved from one device and added to another device, or may be included in both devices.

Figure 10:
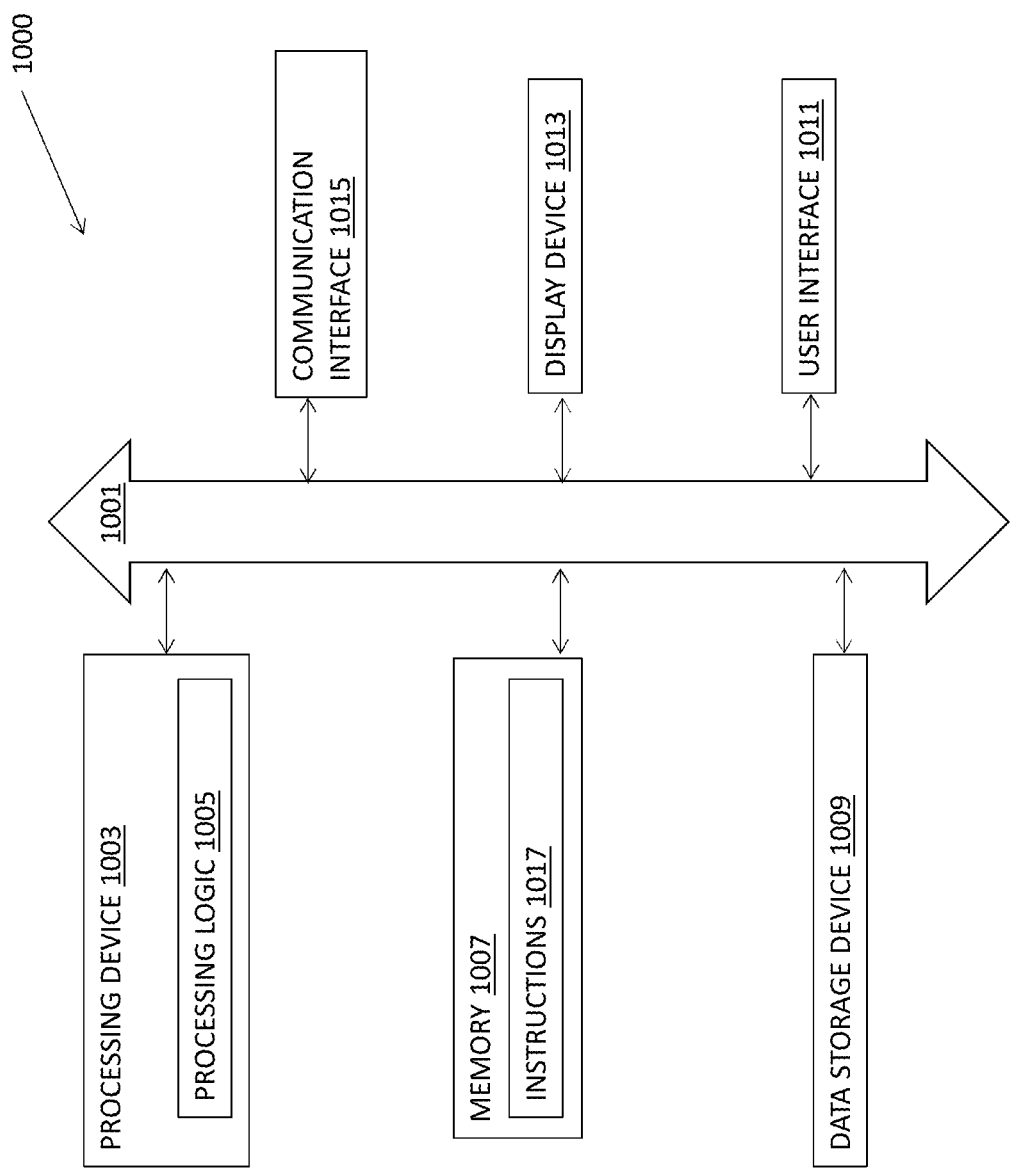
FIG. 10 illustrates a computer system for use in accordance with an embodiment of the present disclosure.

FIG. 10 illustrates a computer system for use in accordance with an embodiment of the present disclosure. In particular, FIG. 10 is a system diagram for a computing device used in a system built in accordance with an embodiment of the present disclosure. FIG. 10 illustrates a functional block diagram of a machine in the example form of computer system 1000, within which a set of instructions for causing the machine to perform any one or more of the methodologies, processes or functions discussed herein may be executed. In some examples, the machine may be connected (e.g., networked) to other machines as described above. The machine may operate in the capacity of a server or a client machine in a client-server network environment, or as a peer machine in a peer-to-peer (or distributed) network environment. The machine may be any special-purpose machine capable of executing a set of instructions (sequential or otherwise) that specify actions to be taken by that machine for performing the functions describe herein. Further, while only a single machine is illustrated, the term "machine" shall also be taken to include any collection of machines that individually or jointly execute a set (or multiple sets) of instructions to perform any one or more of the methodologies discussed herein. In some examples, the platform 100 and server systems of FIG. 1 may be implemented by the example machine shown in FIG. 10 (or a combination of two or more of such machines).

Example computer system 1000 may include processing device 1003, memory 1007, data storage device 1009 and communication interface 1015, which may communicate with each other via data and control bus 1001. In some examples, computer system 1000 may also include display device 1013 and/or user interface 1011.

Processing device 1003 may include, without being limited to, a microprocessor, a central processing unit, an application specific integrated circuit (ASIC), a field programmable gate array (FPGA), a digital signal processor (DSP) and/or a network processor. Processing device 1003 may be configured to execute processing logic 1005 for performing the operations described herein. In general, processing device 1003 may include any suitable special-purpose processing device specially programmed with processing logic 1005 to perform the operations described herein.

Memory 1007 may include, for example, without being limited to, at least one of a read-only memory (ROM), a random access memory (RAM), a flash memory, a dynamic RAM (DRAM) and a static RAM (SRAM), storing computer-readable instructions 1017 executable by processing device 1003. In general, memory 1007 may include any suitable non-transitory computer readable storage medium storing computer-readable instructions 1017 executable by processing device 1003 for performing the operations described herein. Although one memory device 1007 is illustrated in FIG. 10, in some examples, computer system 1000 may include two or more memory devices (e.g., dynamic memory and static memory).

Computer system 1000 may include communication interface device 1011, for direct communication with other computers (including wired and/or wireless communication), and/or for communication with network. In some examples, computer system 1000 may include display device 1013 (e.g., a liquid crystal display (LCD), a touch sensitive display, etc.). In some examples, computer system 1000 may include user interface 1011 (e.g., an alphanumeric input device, a cursor control device, etc.).

In some examples, computer system 1000 may include data storage device 1009 storing instructions (e.g., software) for performing any one or more of the functions described herein. Data storage device 1009 may include any suitable non-transitory computer-readable storage medium, including, without being limited to, solid-state memories, optical media and magnetic media.

Although the present disclosure may provide a sequence of steps, it is understood that in some embodiments, additional steps may be added, described steps may be omitted, and the like. Additionally, the described sequence of steps may be performed in any suitable order.

While illustrative embodiments have been described herein, the scope thereof includes any and all embodiments having equivalent elements, modifications, omissions, combinations (e.g., of aspects across various embodiments), adaptations and/or alterations as would be appreciated by those in the art based on the present disclosure. For example, the number and orientation of components shown in the exemplary systems may be modified.

Thus, the foregoing description has been presented for purposes of illustration. It is not exhaustive and is not limiting to the precise forms or embodiments disclosed.

Modifications and adaptations will be apparent to those skilled in the art from consideration of the specification and practice of the disclosed embodiments.

The invention claimed is:

1. A method for generating improved medical image reports comprising:
   training an artificial intelligence module comprising a convolutional neural network based on radiologist marked image data;
   training a natural language processing module on radiology related text, wherein the natural language processing module comprises at least one recurrent neural network and sentiment analysis;
   receiving medical images and textual data, wherein the textual data comprises a medical image report corresponding to the received medical images;
   generating enhanced medical image data by applying the trained artificial intelligence module to the received medical images to identify suspected abnormalities in the received medical images;
   generating structured text data by applying the trained natural language processing module to the received textual data, wherein the structured text data comprises stratified, categorized and annotated statements regarding patient procedures and conditions;
   generating one or more missed findings by determining discrepancies between suspected abnormalities identified in the generated enhanced medical image data and generated structured text data that are not present in the received textual data;
   providing an alert to at least one of a user or a creator of the medical image report responsive to generating at least one missed finding; and
   providing a proposed improved medical image report to the user or creator of the medical image report, wherein the proposed improved medical image report comprises the received medical image report supplemented with a color-coded presentation of the structured text corresponding to the missed finding.

2. The method of claim 1, wherein the artificial intelligence module comprises at least one of:
   a regression convolutional neural network, a semantic segmentation convolutional network and a classification convolutional neural network.

3. The method of claim 1, comprising:
   generating at least one of a clinical or non-clinical interface including the enhanced medical image data.

4. The method of claim 1, comprising:
   incorporating the enhanced medical image data into an electronic healthcare record.

5. The method of claim 1, wherein providing a proposed improved medical image report comprises:
   identifying and storing each finding indicated in the enhanced medical image data;
   correlating each finding to its corresponding structured text data;
   identifying corresponding portions for each finding in a radiology report;
   identifying discrepancies between the corresponding portions and the corresponding structured text data for each finding; and
   generating improved medical image reports by augmenting the radiology report with the identified discrepancies.

6. The method of claim 5, further comprising:
   presenting the generated improved medical image report to a physician for approval.

7. A system for generating improved medical image reports comprising:
   a server system configured to receive medical images and textual data, wherein the server system comprises:
      an image processing unit configured to:
         train an artificial intelligence module comprising a convolutional neural network based on radiologist marked image data; and
         apply the trained artificial intelligence module to the received medical images to generate enhanced medical image data that identifies suspected abnormalities in the received medical images;
      a text processing unit configured to:
         train a natural language processing algorithm on radiology related text, wherein the natural language processing algorithm comprises at least one recurrent neural network and sentiment analysis; and
         apply the trained natural language processing to the received textual data to generate structured text data, wherein the structured text data comprises stratified, categorized and annotated statements regarding patient procedures and conditions; and
      a platform configured to:
         generate one or more missed findings by determining discrepancies between suspected abnormalities identified in the generated enhanced medical image data and generated structured text data that are not present in the received textual data;
         generate an alert responsive to generating one or more missed findings; and
         provide a proposed improved medical image report to a user or creator of the medical image report, wherein the proposed improved medical image report comprises the received medical image report supplemented with a color-coded presentation of the structured text corresponding to the missed finding.

8. The system of claim 7, wherein the server system comprises a case manager configured to dispatch data and receive results from the image processing unit and the text processing unit.

9. The system of claim 7, wherein, the server system comprises a platform configured to generate at least one of a clinical or non-clinical interface including the enhanced medical image data.

10. The system of claim 9, wherein the platform is configured to incorporate the enhanced medical image data into an electronic healthcare record.

11. A non-transitory computer-readable medium storing instructions that, when executed on one or more processors, cause the one or more processors to:
    train an artificial intelligence module comprising a convolutional neural network based on radiologist marked image data;
    train a natural language processing module on radiology related text, wherein the natural language processing module comprises at least one recurrent neural network and sentiment analysis;
    receive medical images;
    receive textual data comprising a medical image report corresponding to the received medical images;
    generate enhanced medical image data by applying the trained artificial intelligence module to the received medical images to identify suspected abnormalities in the received medical images;

generate structured text data by applying the natural language processing module to the received textual data, wherein the structured text data comprises stratified, categorized and annotated statements regarding patient procedures and conditions;

generate one or more missed findings by determining discrepancies between suspected abnormalities identified in the generated enhanced medical image data and generated structured text data that are not present in the received textual data;

generate an alert responsive to generating one or more missed findings; and generate a proposed improved medical image report comprising the received medical image report supplemented with a color-coded presentation of the structured text corresponding to the missed findings.

12. The non-transitory computer-readable medium of claim 11, wherein the one or more processors is further configured to:

generate at least one of a clinical or non-clinical interface including the enhanced medical image data.

13. The non-transitory computer-readable medium of claim 11, wherein the one or more processors is further configured to:

incorporate the enhanced medical image data into an electronic healthcare record.

14. The non-transitory computer-readable medium of claim 11, wherein generating an alert comprises the one or more processors being configured to:

identify and store each finding indicated in the enhanced medical image data;

correlate each finding to its corresponding structured text data;

identify corresponding portions for each finding in a radiology report;

identify discrepancies between the corresponding portions and the corresponding structured text data for each finding; and generate improved medical image reports by augmenting the radiology report with the identified discrepancies.

* * * * *